(12) United States Patent
Den Boef et al.

(10) Patent No.: US 7,480,050 B2
(45) Date of Patent: Jan. 20, 2009

(54) LITHOGRAPHIC SYSTEM, SENSOR, AND METHOD OF MEASURING PROPERTIES OF A SUBSTRATE

(75) Inventors: Arie Jeffrey Den Boef, Waalre (NL); Wilhelmus Maria Corbeij, Eindhoven (NL); Mircea Dusa, Campbell, CA (US); Reinder Teun Plug, Eindhoven (NL)

(73) Assignee: ASML Netherlands B.V., Veldhoven (NL)

( * ) Notice: Subject to any disclaimer, the term of this patent is extended or adjusted under 35 U.S.C. 154(b) by 84 days.

(21) Appl. No.: 11/350,279

(22) Filed: Feb. 9, 2006

(65) Prior Publication Data

US 2007/0182964 A1    Aug. 9, 2007

(51) Int. Cl.
*G01J 4/00*    (2006.01)
(52) U.S. Cl. .................. 356/364; 356/237.2; 356/364; 356/369
(58) Field of Classification Search ... 356/237.2–237.4, 356/364, 369
See application file for complete search history.

(56) References Cited

U.S. PATENT DOCUMENTS

| | | | |
|---|---|---|---|
| 5,703,692 A | 12/1997 | McNeil et al. | 356/445 |
| 5,880,838 A | 3/1999 | Marx et al. | 356/351 |
| 5,963,329 A | 10/1999 | Conrad et al. | 356/372 |
| 6,608,690 B2 | 8/2003 | Niu et al. | 356/635 |
| 6,699,624 B2 | 3/2004 | Niu et al. | 430/5 |
| 6,704,661 B1 | 3/2004 | Opsal et al. | 702/27 |
| 6,721,691 B2 | 4/2004 | Bao et al. | 702/189 |
| 6,738,138 B2 | 5/2004 | Wei | 356/369 |
| 6,753,961 B1 | 6/2004 | Norton et al. | 356/364 |
| 6,768,983 B1 | 7/2004 | Jakatdar et al. | 706/46 |
| 6,772,084 B2 | 8/2004 | Bischoff et al. | 702/127 |
| 6,782,337 B2 * | 8/2004 | Wack et al. | 356/369 |
| 6,785,638 B2 | 8/2004 | Niu et al. | 702/189 |
| 6,813,034 B2 | 11/2004 | Rosencwaig et al. | 356/601 |
| 6,819,426 B2 | 11/2004 | Sezginer et al. | 356/401 |
| 6,856,408 B2 | 2/2005 | Raymond | 356/601 |
| 6,919,964 B2 | 7/2005 | Chu | 356/601 |
| 6,928,628 B2 | 8/2005 | Seligson et al. | 716/4 |
| 6,961,116 B2 * | 11/2005 | Den Boef et al. | 356/400 |
| 6,972,852 B2 | 12/2005 | Opsal et al. | 356/625 |
| 6,974,962 B2 | 12/2005 | Brill et al. | 250/548 |
| 6,987,572 B2 | 1/2006 | Lakkapragada et al. | 356/601 |
| 7,046,376 B2 | 5/2006 | Sezginer | 356/601 |
| 7,061,615 B1 | 6/2006 | Lowe-Webb | 356/401 |
| 7,061,623 B2 | 6/2006 | Davidson | 356/497 |
| 7,061,627 B2 | 6/2006 | Opsal et al. | 356/601 |
| 7,068,363 B2 | 6/2006 | Bevis et al. | 356/237.5 |
| 7,256,871 B2 * | 8/2007 | Loopstra et al. | 355/72 |
| 2004/0119970 A1 | 6/2004 | Dusa et al. | 356/237.1 |
| 2005/0259324 A1 * | 11/2005 | Flagello et al. | 359/486 |
| 2006/0033921 A1 | 2/2006 | Den Boef et al. | 356/446 |
| 2006/0066855 A1 | 3/2006 | Den Boef et al. | 356/401 |
| 2006/0126074 A1 | 6/2006 | Van Der Werf et al. | 356/489 |
| 2006/0139592 A1 | 6/2006 | Den Boef et al. | 355/53 |

* cited by examiner

*Primary Examiner*—L. G Lauchman
*Assistant Examiner*—Iyabo S Alli
(74) *Attorney, Agent, or Firm*—Sterne, Kessler, Goldstein & Fox P.L.L.C

(57) ABSTRACT

A sensor measuring properties of a substrate in which radiation is projected onto the substrate by a radiation projector that has a first part configured such that the radiation projection can project onto the substrate linearly polarized radiation oriented in a first direction and a second part configured such that the radiation projector can project onto the substrate linearly polarized radiation oriented in a second direction orthogonal to the first direction.

22 Claims, 7 Drawing Sheets

LITHOGRAPHIC SYSTEM, SENSOR, AND METHOD OF MEASURING PROPERTIES OF A SUBSTRATE

BACKGROUND OF THE INVENTION

1. Field of the Invention

The present invention relates to a lithographic system, a sensor and a method for measuring properties of a substrate.

2. Description of the Related Art

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g. including part of, one, or several dies) on a substrate (e.g. a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include steppers, in which each target portion is irradiated by exposing an entire pattern onto the target portion at one time, and scanners, in which each target portion is irradiated by scanning the pattern through a radiation beam in a given direction (the "scanning" direction) while synchronously scanning the substrate parallel or anti-parallel to this direction. It is also possible to transfer the pattern from the patterning device to the substrate by imprinting the pattern onto the substrate.

Sensors are known for inspecting substrates during or after lithographic processes. For example, after a resist on a substrate is developed (having been exposed by a patterned beam of radiation, for example) a measurement and inspection step may be performed. This is referred to as "in-line" because it is carried out in the normal course of processing substrates used in production. This may serve two purposes. Firstly, it is desirable to detect any areas where the pattern in the developed resist is faulty. If a sufficient number of dies on a substrate, namely portions of the substrate that will be used to form an individual device are faulty, the substrate can be stripped of the patterned resist and re-exposed, hopefully correctly, rather than making the fault permanent by carrying out a subsequent process step, for example an etch, with a faulty pattern. Secondly, the measurements may allow errors in the lithographic apparatus, for example illumination settings or exposure dose, to be detected and correct for subsequent exposures. However, many errors in the lithographic apparatus cannot easily be detected or quantified from the patterns printed in resist. Detection of a fault does not always lead directly to its cause. Thus, a variety of "off-line" procedures for detecting and measuring errors in a lithographic apparatus are also known. This may involve replacing the substrate with a measuring device or carrying out exposures of special test patterns, for example at a variety of different machine settings. Such off-line techniques take time, often a considerable amount, during which the end products of the apparatus will be of an unknown quality until the measurement results are made available. Therefore, in-line techniques, ones which can be carried out at the same time as production exposures, for detecting and measuring errors in the lithographic apparatus, are preferred.

Scatterometry is one example of an optical metrology technique that can be used for in-line measurements of CD and overlay. There are two main scatterometry techniques:

1) Spectroscopic scatterometry measures the properties of scattered light at a fixed angle as a function of wavelength, usually using a broadband light source such as Xenon, Deuterium, or a Halogen based light source. The fixed angle can be normally incident or obliquely incident.
2) Angle-resolved scatterometry measures the properties of scattered light at a fixed wavelength as a function of angle of incidence, usually using a laser as a single wavelength light source.

The structure giving rise to a reflection spectrum is reconstructed, e.g. using real-time regression or by comparison to a library of patterns derived by simulation. Reconstruction involves minimization of a cost function. Both approaches calculate the scattering of light by periodic structures. The most common technique is Rigorous Coupled-Wave Analysis (RCWA), though light scattering can also be calculated by other techniques such as FDTD or Integral Equation techniques.

Scatterometry can also be used to inspect features formed after an etch process (which may, for example, have been controlled by a pattern formed by a lithographic process) or to measure the thickness or properties of one or more layers of material formed in a stack.

In order to perform scatterometry measurements, the substrate is illuminated with radiation. In order to obtain the most information from the measurements, the radiation illuminating the substrate may be linearly polarized. The orientation of the polarization should be adjusted to be appropriate for each target on the wafer. In order to provide this, it is presently known to provide a rotating polarizer between the last optical element of the system projecting radiation onto the substrate and the substrate.

However, use of a rotating polarizer may reduce the accuracy of the orientation of the polarized radiation relative to the target, reducing the accuracy of measurement. In addition, it may be desirable to illuminate the target with a wide range of incident angles which is not feasible when using a rotating polarizer.

SUMMARY OF THE INVENTION

It is desirable to provide a sensor for measuring properties of a substrate that can illuminate targets on the substrate with an improved accuracy of the polarization of the radiation. It is further desirable to provide such a sensor which may be able to inspect, in-line, substrates without occupying a large amount of space within a lithographic apparatus.

According to an aspect of the invention, there is provided a sensor system for measuring properties of a substrate, including a radiation projector configured to project radiation onto the substrate; and a detector configured to detect the radiation reflected from the substrate, wherein the radiation projector has a first part configured such that the radiation projector can project onto the substrate linearly polarized radiation oriented in a first direction and a second part configured such that the radiation projector can project onto the substrate linearly polarized radiation oriented in a second direction, orthogonal to the first direction.

According to an aspect of the invention, there is provided a lithographic system arranged to transfer a pattern from a patterning device onto a substrate, including such a sensor system.

According to an aspect of the invention, there is provided a method of measuring properties of a substrate, including: projecting radiation onto a substrate using a radiation projector; and detecting radiation reflected from the substrate that is indicative of the properties to be measured, wherein the radiation projector is configured to project onto the substrate linearly polarized radiation oriented in a first direction and linearly polarized radiation oriented in a second direction, orthogonal to the first direction.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION

Figure 1:
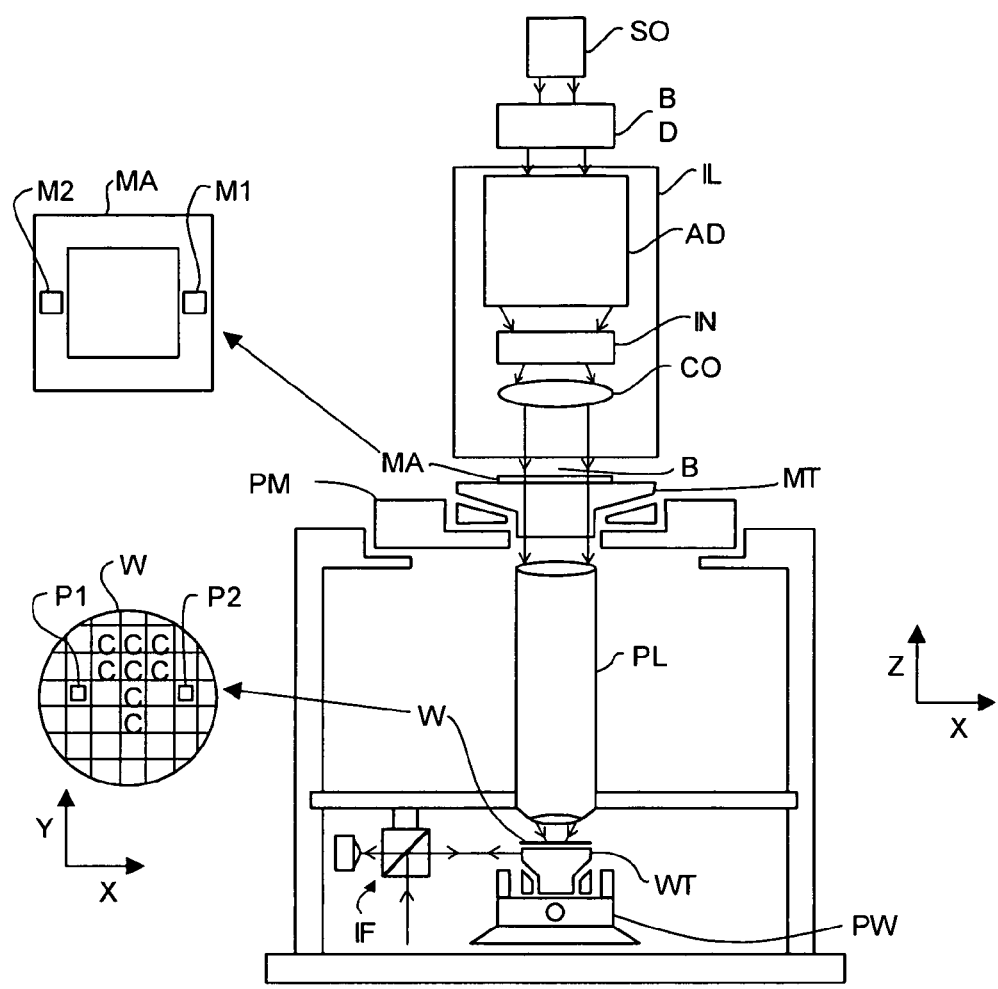
FIG. 1 depicts a lithographic apparatus according to an embodiment of the invention.

FIG. 1 schematically depicts a lithographic apparatus according to one embodiment of the invention. The apparatus includes an illumination system (illuminator) IL configured to condition a radiation beam B (e.g. UV radiation or DUV radiation). A support (e.g. a mask table) MT is configured to support a patterning device (e.g. a mask) MA and is connected to a first positioner PM configured to accurately position the patterning device in accordance with certain parameters. A substrate table (e.g. a wafer table) WT is configured to hold a substrate (e.g. a resist-coated wafer) W and is connected to a second positioner PW configured to accurately position the substrate in accordance with certain parameters. A projection system (e.g. a refractive projection lens system) PL is configured to project a pattern imparted to the radiation beam B by patterning device MA onto a target portion C (e.g. including one or more dies) of the substrate W.

The illumination system may include various types of optical components, such as refractive, reflective, magnetic, electromagnetic, electrostatic or other types of optical components, or any combination thereof, to direct, shape, or control radiation.

The support supports, e.g. bears the weight of, the patterning device. It holds the patterning device in a manner that depends on the orientation of the patterning device, the design of the lithographic apparatus, and other conditions, such as for example whether or not the patterning device is held in a vacuum environment. The support can use mechanical, vacuum, electrostatic or other clamping techniques to hold the patterning device. The support may be a frame or a table, for example, which may be fixed or movable as required. The support may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features and/or assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g. employing a transmissive mask). Alternatively, the apparatus may be of a reflective type (e.g. employing a programmable mirror array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g. water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives radiation from a radiation source SO. The source and the lithographic apparatus may be separate entities, for example when the source is an excimer laser. In such cases, the source is not considered to form part of the lithographic apparatus and the radiation is passed from the source SO to the illuminator IL with the aid of a beam delivery system BD including, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may include an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may include various other components, such as an integrator IN and a condenser CO. The illuminator may be used to condition the radiation beam, to have a desired uniformity and intensity distribution in its cross-section.

The radiation beam B is incident on the patterning device (e.g., mask MA), which is held on the support (e.g., mask table MT), and is patterned by the patterning device. Having traversed the mask MA, the radiation beam B passes through the projection system PL, which focuses the beam onto a target portion C of the substrate W. With the aid of the second positioner PW and position sensor IF (e.g. an interferometric device, linear encoder or capacitive sensor), the substrate table WT can be moved accurately, e.g. so as to position different target portions C in the path of the radiation beam B. Similarly, the first positioner PM and another position sensor (which is not explicitly depicted in FIG. 1, but which may be an interferometric device, linear encoder or capacitive sensor) can be used to accurately position the mask MA with respect to the path of the radiation beam B, e.g. after mechanical retrieval from a mask library, or during a scan. In general, movement of the mask table MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the mask table MT may be connected to a short-stroke actuator only, or may be fixed. Mask MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the mask MA, the mask alignment marks may be located between the dies.

The depicted apparatus could be used in at least one of the following modes:

1. In step mode, the mask table MT and the substrate table WT are kept essentially stationary, while an entire pattern imparted to the radiation beam is projected onto a target portion C at one time (i.e. a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the mask table MT and the substrate table WT are scanned synchronously while a pattern imparted to the radiation beam is projected onto a target portion C (i.e. a single dynamic exposure). The velocity and direction of the substrate table WT relative to the mask table MT may be determined by the (de-)magnification and image reversal characteristics of the projection system PL. In scan mode, the maximum size of the exposure field limits the width (in the non-scanning direction) of the target portion in a single dynamic exposure, whereas the length of the scanning motion determines the height (in the scanning direction) of the target portion.

3. In another mode, the mask table MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2:
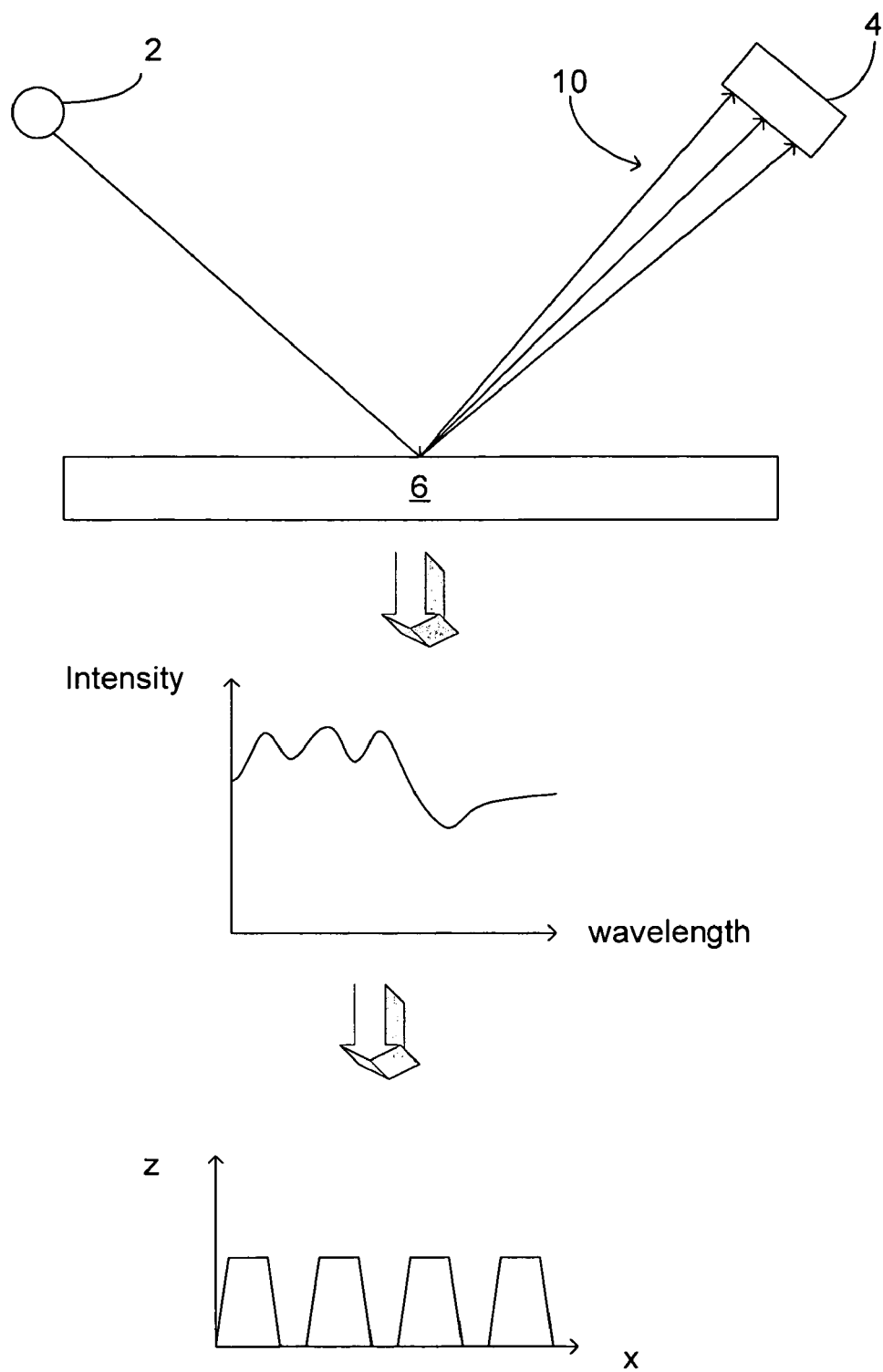
FIG. 2 depicts a scatterometer that may be used as a sensor in the present invention.

The properties of the surface of a substrate W may be determined using a sensor such as a scatterometer such as that depicted in FIG. 2. The scatterometer includes a broadband (white light) radiation projector 2 which projects radiation onto a substrate 6. The reflected radiation is passed to a spectrometer detector 4, which measures a spectrum 10 (intensity as a function of wavelength) of the specular reflected radiation. From this data, the structure or profile giving rise to the detected spectrum may be reconstructed, e.g. by Rigorous Coupled Wave Analysis and non-linear regression or by comparison with a library of simulated spectra as shown at the bottom of FIG. 2. In general, for the reconstruction the general form of the structure is known and some parameters are assumed from knowledge of the process by which the structure was made, leaving only a few parameters of the structure to be determined from the scatterometry data.

The scatterometer may be a normal-incidence scatterometer or an oblique-incidence scatterometer. Variants of scatterometry may also be used in which the reflection is measured at a range of angles of a single wavelength, rather than the reflection at a single angle of a range of wavelengths.

Figure 3:
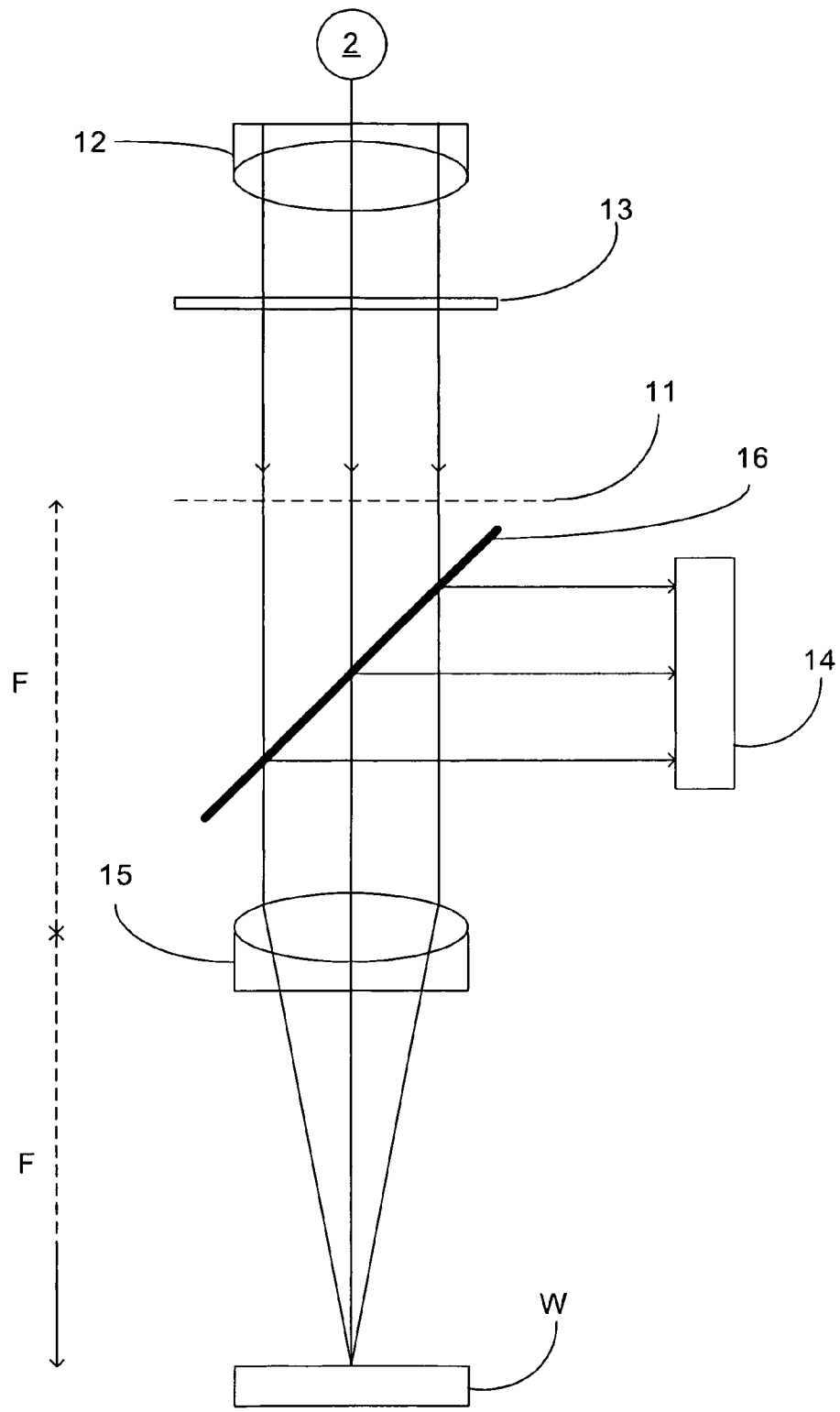
FIG. 3 depicts the general operating principle of measuring an angle resolved spectrum in the pupil plane of a high-NA lens.

Scatterometers for measuring properties of a substrate may measure, in the pupil plane 11 of a high numerical aperture lens, the properties of an angle-resolved spectrum reflected from the substrate surface at a plurality of angles and wavelengths as shown in FIG. 3. Such a scatterometer may include a radiation projector 2 for projecting radiation onto the substrate and a detector 14 configured to detect the reflected spectra. The pupil plane is the plane in which the radial position of radiation defines the angle of incidence and the angular position defines azimuth angle of the radiation. The detector 14 is placed in the pupil plane of the high numerical aperture lens. The numerical aperture may be high, for example at least 0.9, or at least 0.95. Immersion scatterometers may even have lenses with numerical apertures greater than 1.

Some angle-resolved scatterometers only measure the intensity of scattered light. However, more recent scatterometers allow several wavelengths to be measured simultaneously at a range of angles. The properties measured by the scatterometer for different wavelengths and angles may be the intensity of transverse magnetic- and transverse electric-polarized light and the phase difference between the transverse magnetic- and transverse electric-polarized light.

Using a broadband light source (i.e. one with a wide range of light frequencies or wavelengths, and therefore of colors) is possible, which gives a large etendue, allowing the mixing of multiple wavelengths. The plurality of wavelengths in the broadband preferably each has a bandwidth of, for example, δλ, and a spacing, therefore, of at least 2δλ (i.e. twice the wavelength). Several "sources" of radiation can be different portions of an extended radiation source which have been split using, for example, fiber bundles. In this way, angle resolved scatter spectra can be measured at multiple wavelengths in parallel. A 3-D spectrum (wavelength and two different angles) is measured, which contains more information than a 2-D spectrum. This allows more information to be measured which increases metrology process robustness.

A scatterometer that may be used with the present invention is shown in FIG. 3. The radiation of the radiation projector 2 is focused using lens system 12 through interference filter 13 and is focused onto substrate W via a microscope objective lens 15. The radiation is then reflected via partially reflective surface 16 into a detector in the back projected pupil plane 11 in order to have the scatter spectrum detected. The pupil plane 11 is at the focal length of the lens system 15. A detector and high aperture lens are placed at the pupil plane. The pupil plane may be re-imaged with auxiliary optics since the pupil plane of a high-NA lens is usually located inside the lens.

The pupil plane of the reflected radiation is imaged on the CCD detector with an integration time of, for example, 40 milliseconds per frame. In this way, a two-dimensional angular scatter spectrum of the substrate targets is imaged on the detector. The detector may be, for example, an array of CCD detectors or CMOS detectors.

A set of interference filters 13 is available to select a wavelength of interest in the range of, say, 405-790 nm or even lower, such as 200-300 nm. The interference filter may be tunable rather than including a set of different filters. A grating could be used instead of interference filters.

The substrate W, or even the partially reflective surface 14, may be a grating. The grating may be printed such that after development, the bars are formed of solid resist lines. The bars may alternatively be etched into the substrate. This pattern is sensitive to chromatic aberrations in the lithographic projection apparatus, particularly the projection system PL, and illumination symmetry and the presence of such aberrations will manifest themselves in a variation in the printed grating. Accordingly, the scatterometry data of the printed gratings is used to reconstruct the gratings. The parameters of the grating, such as line widths and shapes, may be input to the reconstruction process from knowledge of the printing step and/or other scatterometry processes.

Figure 4A:
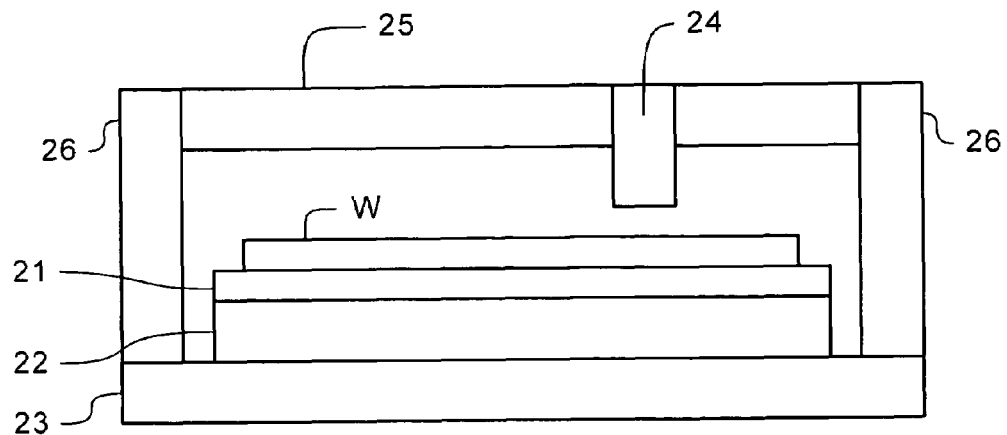
FIGS. 4a and 4b depict an embodiment of the present invention.
Figure 4B:
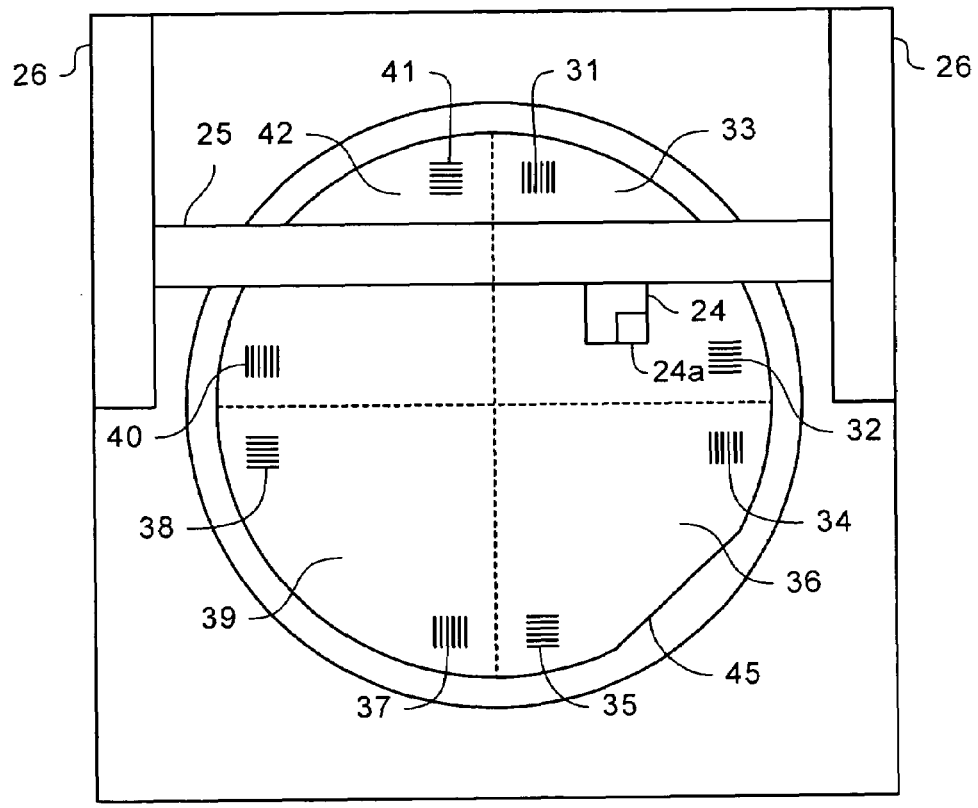

FIGS. 4a and 4b depict the configuration of a sensor according to an embodiment of the present invention. It should be appreciated that, although the description below relates to the use of such a sensor within a lithographic system, the present invention is not so limited and the sensor arrangement of the invention may be provided as a "stand alone" unit or as part of another apparatus. As shown, the substrate W is mounted on a substrate support or chuck 21. This in turn is mounted by an actuator 22 on the base 23 of the apparatus. The actuator 22 is configured such that it can rotate the substrate support 21 and therefore the substrate W, relative to the base 23 about an axis perpendicular to the surface of the substrate W.

The radiation projector for projecting radiation onto the substrate and the detector configured to detect the radiation reflected from the substrate, for example a scatterometer as discussed above, are mounted in a sensing unit 24. The sensing unit 24 is mounted to the base 23 by an actuator system that is configured to move the sensing unit 24 relative to the substrate W without rotating the substrate W using the rotary actuator 22.

In the arrangement depicted in FIGS. 4a and 4b, the actuator system consists of a gantry 25, mounted to supports 26 that support the gantry 25 above the substrate W. The gantry 25 is mounted to the support 26 in such a manner that the gantry 25 can be moved in a linear direction parallel to the surface of the substrate W. The sensing unit 24 is mounted to the gantry 25 such that the sensing unit can be moved along the gantry 25 in a second linear direction, parallel to the surface of the substrate W but perpendicular to the direction of movement of the gantry. Accordingly, it is possible to control the position of the sensing unit 24 relative to the substrate W independently in two orthogonal directions. Consequently, the sensing unit 24 may be positioned to any required location relative to the substrate W within a defined range of movement without rotating the substrate W relative to the base 23 using the rotary actuator 22.

It should be appreciated that variations of the actuator system discussed above may be used. For example, the position of the gantry 25 may be fixed and instead an actuator may be provided to move the substrate support 21 in a direction perpendicular to the length of the gantry.

The sensing unit 24, as discussed in more detail below, includes a radiation projector configured to project radiation onto the substrate and has a first part configured such that the radiation projector can project onto the substrate linearly polarized radiation oriented in a first direction and second part configured such that the radiation projection can project onto the substrate linearly polarized radiation oriented in a second direction, orthogonal to the first direction. Accordingly, it is possible to inspect targets on the substrate both when illuminated by linearly polarized radiation oriented in a first direction and when illuminated by linearly polarized radiation oriented in a direction orthogonal to the first direction. Furthermore, because the radiation projector has two separate parts dedicated to projecting linearly polarized radiation oriented in orthogonal directions, the accuracy of the system compared to one in which the polarization is provided by a rotating polarizer is greatly improved. For example, in many cases, useful information may be obtained by the difference between the signals received by the detector when the target is illuminated by the orthogonally oriented linearly polarized radiation. In situations in which the difference is small, the effect may be concealed in a system in which a rotating polarizer is used. However, in a system such as the present invention in which separate parts are dedicated to providing the orthogonally oriented linearly polarized radiation, this inaccuracy may be removed. Furthermore, the system is simpler and therefore cheaper because there is no requirement to provide a system for accurately controlling the rotation of the polarizer. A further advantage of the system of the present invention is that the sensor can switch between inspecting the target, with radiation of the orthogonal polarizations more quickly than if a component such as a polarizer needs to be rotated accurately.

As discussed above, the sensing unit 24 may be moved by its actuator system to inspect targets at different locations on the substrate W. For desired results, it may be desirable to illuminate the targets on the substrate W with the linearly polarized radiation oriented at a given angle relative to the target. This may be achieved according to the invention by rotating the substrate W using the rotary actuator 22 such that the target on the substrate W is at the required orientation relative to the linearly polarized radiation projected onto the substrate by the sensing unit 24. The sensing unit 24 may then be positioned relative to the target using its actuator system.

All of the targets on the substrate W may be oriented such that the desired orientation of the linearly polarized radiation illuminating them is parallel or perpendicular to a given direction on the substrate W. For example, the substrate W depicted in FIG. 4b includes targets 31, 32 in a first quadrant 33 of the substrate, targets 34, 35 in a second quadrant 36 of the substrate, targets 37, 38 in a third quadrant 39 of the substrate and targets 40, 41 in a fourth quadrant 42 of the substrate W. Each of the targets in this case are formed from gratings including striations parallel or perpendicular to a single direction on the substrate.

In order to reduce the amount of space required by the sensor in, for example, a lithographic apparatus, the range of movement of the sensing unit 24 may be limited to only cover a single quadrant of the substrate W. For example, in the arrangement depicted in FIG. 4b, the sensing unit 24 may be limited to movement only within the area corresponding to the first quadrant 33 of the substrate W in its position depicted in FIG. 4b. In order to inspect targets within the second quadrant 36 of the substrate W, the substrate W may be rotated by the rotary actuator 22 counter clockwise through 90° such that the second quadrant 36 takes the place of the first quadrant 33 of the substrate, namely is located within the area within which the sensing unit 24 may be moved. The targets 34, 35 within the second quadrant 36 will still be illuminated by radiation that is linearly polarized with an optimum orientation because all of the targets in the second quadrant 36 are optimally illuminated by radiation that is linearly polarized in an orientation parallel to or perpendicular to the optimum orientation for the targets in the first quadrant 33 and because the sensing unit 24 has dedicated parts providing orthogonally oriented linearly polarized radiation.

The rotary actuator 22 may be configured solely to accurately rotate the substrate W by rotation of multiples of 90° in order successively to bring each of the quadrants 33,36,39,42 of the substrate W within the range of movement of the sensing unit 24. It should be appreciated, however, that the rotary actuator 22 may be configured to accurately rotate the substrate W through any angle. This may be used, for example, in order to initially orient the substrate such that a first set of metrology targets are at the required orientation to be optimally illuminated by the sensing unit 24 (after which the substrate may be rotated by multiples of 90°).

In order to determine the initial orientation of the substrate W, the sensing unit 24 may include a detector 24a for inspecting a notch or a flat 45 on one side of the substrate W. Such a notch or flat 45 may be located in order to identify the orientation of the substrate which, in turn, may be used to determine the orientation of the metrology targets if these are provided at a known orientation relative to the position of the notch or flat 45 on the substrate W. It should be appreciated that the detector 24a for inspecting a notch or a flat 45 on the substrate in order to determine the orientation of the substrate need not be part of the sensing unit 24 but may be separately mounted within the lithographic apparatus, for example.

Alternatively or additionally, the initial orientation of the substrate W may be determined by visual inspection of the metrology targets formed on the substrate and/or device structures already formed on the substrate. This visual inspection may be performed by the sensing unit 24, for example using a CCD detector also used to inspect the metrology targets. Alternatively or additionally, a dedicated visual inspection tool such as a camera or a further CCD device may be provided, for example as part of or separate from the sensing unit 24.

It should be appreciated that alternative actuator systems to those described above and depicted in FIGS. 4a and 4b may be used to rotate the substrate W relative to the base 23 and/or to move the sensing unit 24 relative to the base 23.

Figure 5:
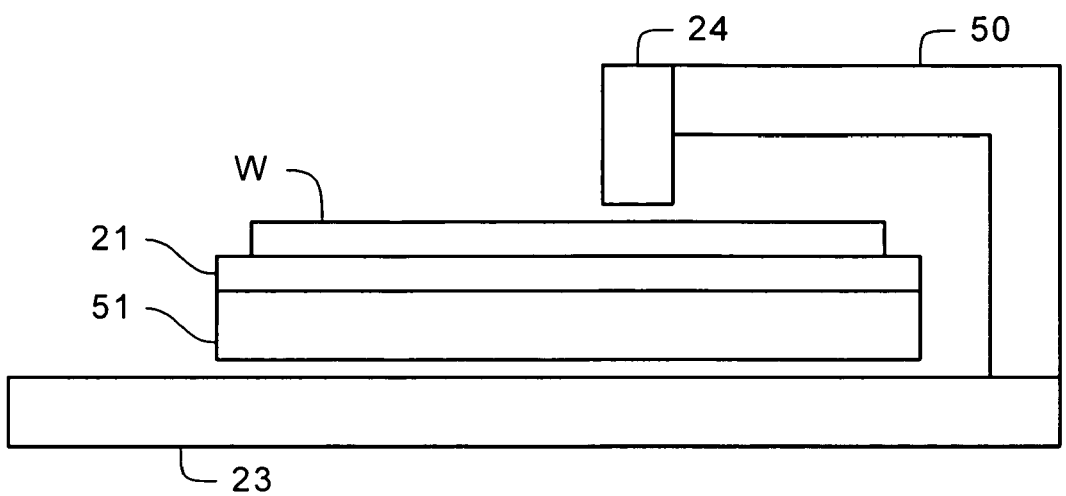
FIG. 5 depicts an embodiment of the present invention.

FIG. 5 depicts an embodiment of the arrangement of the sensor according to the present invention. Much of this embodiment and its operation are the same as the embodiment described above and therefore the description thereof will not be repeated.

In the embodiment, the sensing unit 24 is mounted on a support 50 and arranged at a fixed position relative to the base 23. The substrate W is mounted on a substrate support 21. The position of the substrate support 21, and therefore the substrate W, is controlled by an actuator system 51.

In the system depicted in FIG. 5, the actuator system 51 is a planar motor which is capable of controlling the position of the substrate support 21 linearly in two orthogonal directions parallel to the surface of the substrate W and rotationally about an axis perpendicular to the surface of the substrate. (In general, the planar motor may be able to control the position of the substrate support 21 relative to the base 23 in up to all 6 degrees of freedom). Therefore, the actuator system 51 controls both the position of the sensing unit 24 relative to the substrate W in order to allow the sensing unit 24 to inspect targets at different locations on the substrate, and the orientation of the substrate W relative to the sensing unit 24, in order to provide a desired orientation of the linearly polarized radiation illuminating a metrology target on the substrate W relative to that target.

As before, the actuator system 51 may be configured to rotate the substrate W by multiples of 90° and the range of motion of the substrate relative to the sensing unit 24 may be such that the sensing unit can only inspect metrology targets within a single quadrant of the substrate W without the substrate W being rotated.

It should be appreciated that the actuator system 51 need not be a planar motor but merely provides a system by which the position of the substrate W relative to the base 23 may be controlled linearly in two orthogonal directions parallel to the surface of the substrate and rotationally about an axis perpendicular to the substrate. For example, the actuator system 51 may include: a first linear actuator configured to control the position of a first stage relative to the base 23 in a first direction parallel to the surface of the substrate W; a second linear actuator, mounted on the first stage and configured to control the position of a second stage relative to the first stage in a second direction, parallel to the surface of the substrate W and perpendicular to the first direction; and a third actuator, configured to control the position of the substrate support 21 relative to the second stage rotationally about an axis perpendicular to the substrate W.

Figure 6:
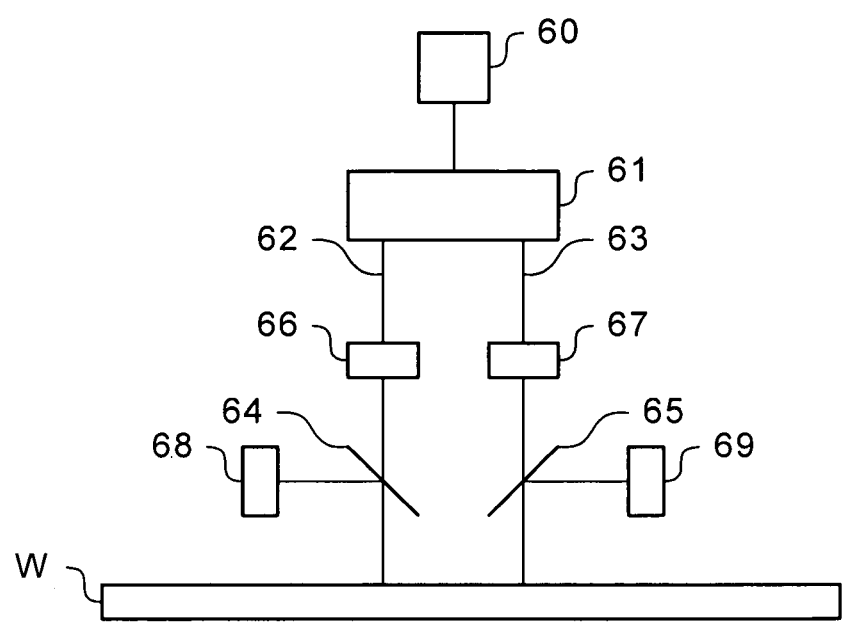
FIG. 6 depicts an embodiment of the present invention.

FIG. 6 depicts a sensing unit that may be used as part of the present invention and, in particular with either of the embodiments discussed above. As depicted, the sensing unit includes a source of radiation 60 that provides the radiation to illuminate the metrology targets on the substrate W. It should be appreciated that the source of radiation 60 may be included within the sensing unit or may be separate from and connected to the sensing unit itself. In the case of a sensing unit used within a lithographic apparatus, the source of radiation may be entirely separate from the lithographic apparatus. In any case, the source of radiation may be connected to the remainder of the sensing unit by, for example, a fiber optic connection.

The embodiment depicted in FIG. 6 further includes an optical switching unit 61, configured to either provide the radiation from the radiation source 60 to a first beam path 62 or a second beam path 63. The optical switching unit 61 may be formed from a reflector or a prism that is rotationally mounted and has its position controlled by an actuator. Alternatively, it may be formed from an appropriately configured component formed from an electro-optical material.

Radiation following the first beam path 62 is polarized by a first linear polarizer 66, passes through a partial reflector 64 and is projected onto the substrate W. Subsequently, reflected radiation is reflected by the partial reflector 64 into a detector

68 in a manner as described above in relation to FIG. 3. Radiation following the second beam path 63 likewise is polarized by a second linear polarizer 67, passes through a second partial reflector 65, reflected by the surface of the substrate W and reflected by the second partial reflector 65 into a second detector 69. It should be appreciated that the arrangement depicted in FIG. 6 is simplified and that, in general, the configuration of the sensor subsequent to the optical switching device 61 may, for each beam path 62, 63 be similar to that described above in relation to FIGS. 2 and 3.

The first and second linear polarizers 66, 67 are configured such that the orientation of the linearly polarized radiation projected onto the substrate from the first linear polarizer 66 is perpendicular to the linearly polarized radiation projected onto the substrate from the second linear polarizer 67. The polarization of the radiation projected onto the substrate may be selected to be eigen-polarizations of the detector, reducing the calibration requirement and improving the accuracy.

Figure 7A:
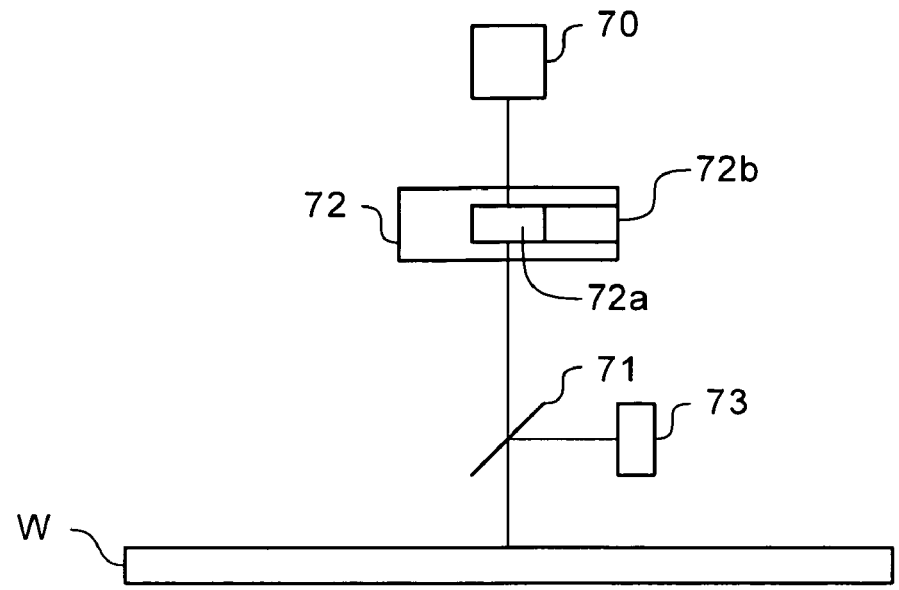
FIGS. 7a and 7b depict an embodiment of the present invention.
Figure 7B:
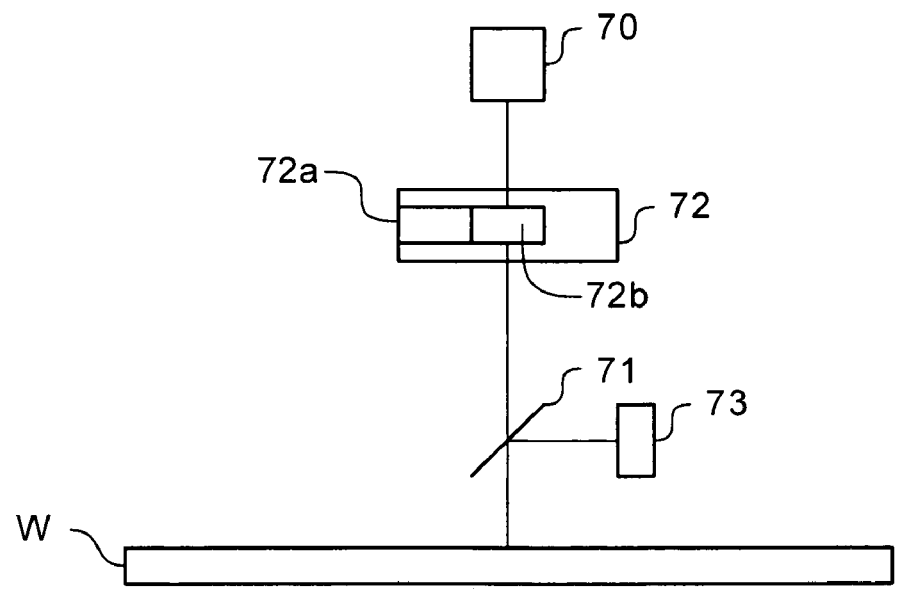

FIGS. 7a and 7b depict an alternative arrangement of a sensing unit that may be used in the present invention, for example in combination with either of the first two embodiments. In comparison to the arrangement of the embodiment of FIG. 6, a single beam path is provided. Accordingly, radiation from the radiation source 70 is linearly polarized in a polarizing unit 72, passes through a partial reflector 71, reflected by the substrate W and, subsequently, by the partial reflector 71 and detected in the detector 73. As before, the arrangement depicted is simplified and it may, in general, include additional components such as those discussed above in relation to FIGS. 2 and 3.

FIG. 7a depicts the sensing unit in a first operating condition and FIG. 7b depicts a sensing unit in a second operating condition. As shown, the polarizing unit 72 includes two linear polarizers 72a, 72b. In the first operating condition, the beam of radiation is linearly polarized by the first linear polarizer 72a. In the second operating condition, the beam of radiation is linearly polarized by the second linear polarizer 72b. The first and second linear polarizers 72a, 72b are configured such that the orientation of the linearly polarized radiation projected onto the substrate W in the first operating condition is perpendicular to the linearly polarized radiation projected onto the substrate W in the second operating condition.

Figure 8:
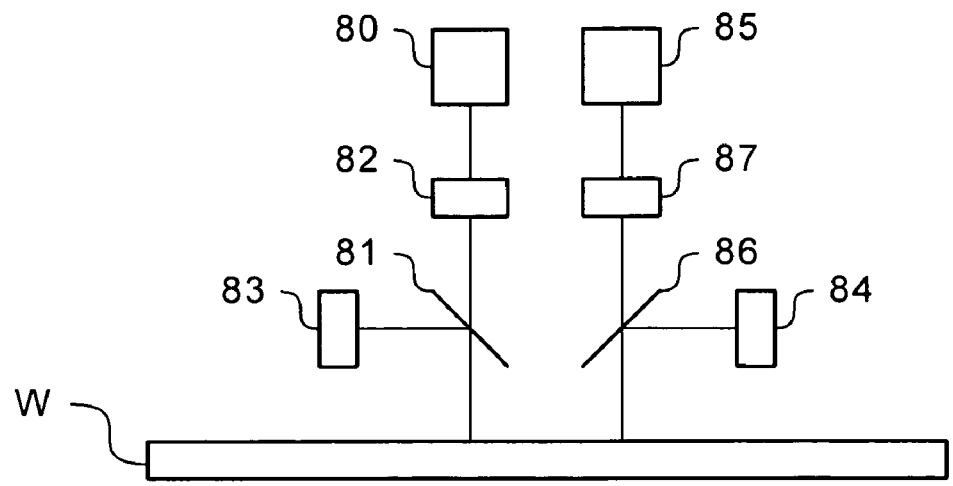
FIG. 8 depicts an embodiment of the present invention.

FIG. 8 depicts a further variation of an arrangement of a sensing unit that may be used in the present invention, for example with either of the first two embodiments. As shown, in this embodiment, the sensing unit has two separate parts. The first part includes a first source 80 or a connection to a first source 80, providing a beam of radiation that is linearly polarized by a first linear polarizer 82 and passes through a partial reflector 81. The radiation is subsequently reflected by the substrate W and the partial reflector 81 and detected by the detector 83. The second part includes a second source 85 or a connection to a second source 85, providing a second beam of radiation that is linearly polarized by a second linear polarizer 87 and passes through a second partial reflector 86. The beam of radiation is subsequently reflected by the substrate W and the second partial reflector 86 and detected by a second detector 84. As before, both parts of the sensing unit depicted are simplifications and, in general, one or both of the parts of the sensing unit may be as described above in relation to FIGS. 2 and 3.

The first and second linear polarizers 82, 87 are configured such that the orientation of the linearly polarized radiation projected onto the substrate W from the first linear polarizer 82 is perpendicular to the orientation of the linearly polarized radiation projected onto the substrate W from the second linear polarizer 87.

Figure 9:
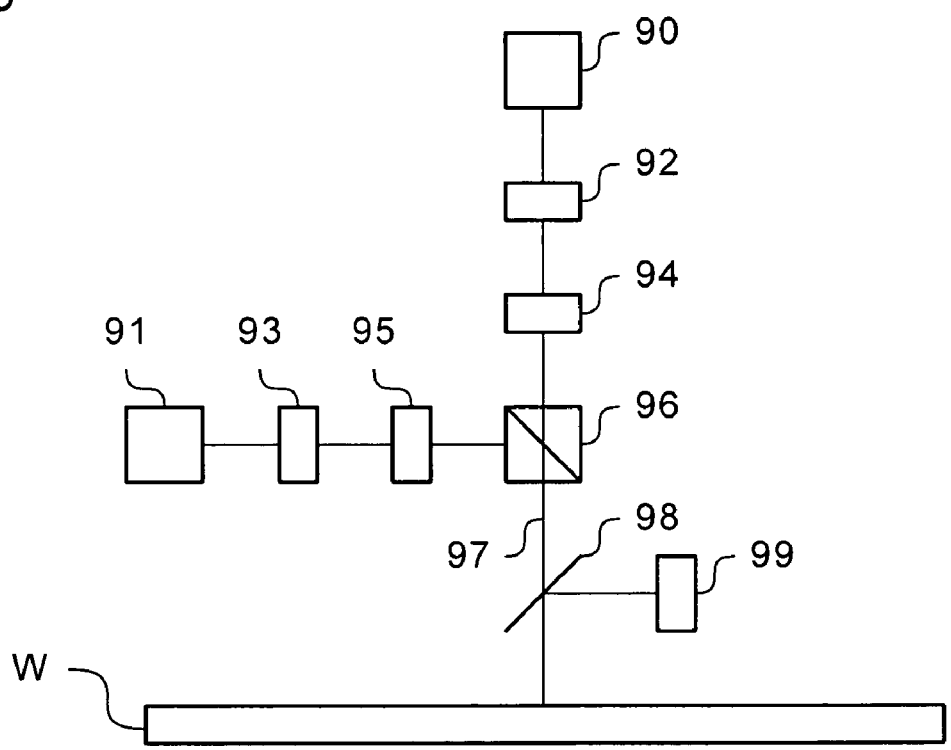
FIG. 9 depicts an embodiment of the present invention.

FIG. 9 depicts a further variation of an arrangement of a sensing unit that may be used in the present invention, for example with either of the first two embodiments. As shown, the sensing unit includes first and second radiation sources 90, 91 or connection to first and second radiation sources 90, 91. The output of the radiation sources is controlled by respective shutters 92, 93.

The radiation from the sources is subsequently linearly polarized by respective linear polarizers 94, 95 and the beam paths for the radiation from the two radiation sources 90, 91 is combined by a beam combiner 96 to a single beam path 97. Thereafter, the sensing unit functions as described before, namely the beam of radiation passes through a partial reflector 98, is reflected by the substrate W and reflected by the partial reflector 98 into the detector 99. As before, the configuration depicted is simplified and, in general, the sensing unit from the point that the beam paths are combined may be as described above in relation to FIGS. 2 and 3.

The linear polarizers 94, 95 are configured such that the orientation of the linearly polarized radiation projected onto the substrate W derived from the first radiation source 90 is perpendicular to the linearly polarized radiation projected onto the substrate W derived from the second radiation source 91.

In a variation of this embodiment and the embodiment of FIG. 8 discussed above, the linear polarizers may be omitted if the radiation sources are white light lasers generating polarized white light and configured to provide the radiation oriented in the required manner. The lasers may be connected to the remainder of the sensing unit using, for example, polarization maintaining photonic crystal fibres.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin-film magnetic heads, etc. It should be appreciated that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it should be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g. having a wavelength of or about 365, 355, 248, 193, 157 or 126 nm) and extreme ultra-violet (EUV) radiation (e.g. having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

While specific embodiments of the invention have been described above, it will be appreciated that the invention may be practiced otherwise than as described. For example, the invention may take the form of a computer program containing one or more sequences of machine-readable instructions describing a method as disclosed above, or a data storage medium (e.g. semiconductor memory, magnetic or optical disk) having such a computer program stored therein.

The descriptions above are intended to be illustrative, not limiting. Thus, it will be apparent to one skilled in the art that modifications may be made to the invention as described without departing from the scope of the claims set out below.

What is claimed is:

1. A sensor system for measuring properties of a substrate, comprising:
   a radiation projector configured to project radiation onto the substrate; and
   a detector configured to detect the radiation reflected from the substrate, wherein the radiation projector has a first part configured such that the radiation projector projects onto the substrate linearly polarized radiation oriented in a first direction and a second part configured such that the radiation projector projects onto the substrate linearly polarized radiation oriented in a second direction, orthogonal to the first direction, wherein the radiation system is configured to output linearly polarized radiation oriented in the first direction or linearly polarized radiation oriented in the second direction.

2. A sensor system according to claim 1, further comprising:
   a first actuator configured to rotate the substrate relative to the radiation projector; and
   a second actuator configured to move the detector relative to the substrate without rotating the substrate relative to the radiation projector.

3. A sensor system according to claim 1, wherein the position and orientation of the radiation projector relative to the detector is fixed.

4. A sensor system according to claim 2, wherein the second actuator is configured to control the position of the detector relative to the substrate independently in two orthogonal directions that are parallel to the plane of the surface of the substrate on which the radiation of the radiation projector is projected.

5. A sensor system according to claim 1, further comprising:
   an actuator configured to rotate the substrate relative to the radiation projector and to move the detector relative to the substrate without rotating the substrate relative to the radiation projector.

6. A sensor system according to claim 2, wherein the first actuator is configured to rotate the substrate relative to the radiation projector by multiples of 90° and the second actuator is configured to have a range of movement such that the detector can detect radiation from any point within a quadrant of the substrate without the substrate rotating relative to the radiation projector.

7. A sensor system according to claim 1, wherein the radiation projector comprises
   a first linear polarizer arranged such that radiation directed to the first linear polarizer is projected onto the substrate linearly polarized and oriented in the first direction; and
   a second linear polarizer arranged such that radiation directed to the second linear polarizer is linearly polarized and oriented in the second direction.

8. A sensor system according to claim 7, wherein the detector comprises a first part configured to detect radiation reflected from the surface of the substrate that is derived from the first linear polarizer; and
   a second part configured to detect radiation reflected from the surface of the substrate that is derived from the second linear polarizer.

9. A sensor system according to claim 7, wherein the radiation projector further comprises a switchable optical element configured to direct radiation from a radiation source such that it can be switched between the first and second linear polarizers.

10. A sensor system according to claim 7, wherein the radiation projector comprises a first radiation source configured to provide radiation to the first linear polarizer and a second radiation source configured to provide radiation to the second linear polarizer.

11. A sensor system according to claim 7, wherein the radiation projector further comprises
    a radiation source; and
    a linear polarizer exchange unit configured to position one of the first and second linear polarizers such that radiation from the radiation source is polarized by said one of the first and second linear polarizers before being projected onto the substrate.

12. A sensor system according to claim 1, wherein the radiation projector includes first and second radiation sources, configured to generate said linearly polarized radiation that is projected onto the substrate oriented in said first and second directions, respectively.

13. A sensor system according to claim 2, wherein the sensor is configured to measure properties of a substrate having a plurality of metrology gratings formed on a surface of the substrate, oriented such that at least one grating is formed of striations arranged parallel to a third direction and at least one grating is formed of striations arranged perpendicular to the third direction, and the sensor is configured to orient the substrate such that, when the radiation projector projects radiation onto the substrate, one of the first and second directions is parallel to the third direction.

14. A sensor system according to claim 13, further comprising a notch locator configured to locate a notch on the edge of a substrate, indicative of the orientation of the substrate, wherein the first actuator orients the substrate based on information from the notch locator in order to ensure that said one of the first and second directions is parallel to the third direction.

15. A sensor system according to claim 13, further comprising a visual inspection tool configured to inspect a metrology target formed on the substrate and device structures formed on the substrate in order to generate information indicative of the orientation of the substrate, wherein the first actuator orients the substrate based on information from the visual inspection tool in order to ensure that said one of the first and second directions is parallel to the third direction.

16. A lithographic system arranged to transfer a pattern from a patterning device onto a substrate, the lithographic system comprising a sensor configured to measure properties of the substrate, the sensor comprising a radiation projector configured to project radiation onto the substrate, and a detector configured to detect the radiation reflected from the substrate, wherein the radiation projector has a first part configured such that the radiation projector projects onto the substrate linearly polarized radiation oriented in a first direction and a second part configured such that the radiation projector projects onto the substrate linearly polarized radiation oriented in a second direction, orthogonal to the first direction, wherein the radiation system is configured to output linearly polarized radiation oriented in the first direction or linearly polarized radiation oriented in the second direction.

17. A method of measuring properties of a substrate, comprising:

projecting radiation onto a substrate using a radiation projector; and detecting, using a detector, radiation reflected from the substrate that is indicative of the properties to be measured, wherein the radiation projector is configured to project onto the substrate linearly polarized radiation oriented in a first direction or linearly polarized radiation oriented in a second direction, orthogonal to the first direction.

18. A method according to claim 17, further comprising rotating the substrate relative to the radiation projector and moving the detector relative to the substrate without rotating the substrate relative to the radiation projector.

19. A method according to claim 18, comprising rotating the substrate relative to the radiation projector by multiples of 90° and moving the detector in a range of movement such that the detector can detect radiation from any point within a quadrant of the substrate without the substrate rotating relative to the radiation projector.

20. A method according to claim 17, comprising measuring properties of a substrate having a plurality of metrology gratings formed on a surface of the substrate, oriented such that at least one grating is formed of striations arranged parallel to a third direction and at least one grating is formed of striations arranged perpendicular to the third direction, and orienting the substrate such that, when the radiation is projection onto the substrate, one of the first and second directions is parallel to the third direction.

21. A method according to claim 20, further comprising locating a notch on the edge of a substrate, indicative of the orientation of the substrate, and orienting the substrate based on information from locating the notch in order to ensure that said one of the first and second directions is parallel to the third direction.

22. A method according to claim 20, further comprising inspecting a metrology target formed on the substrate and device structures formed on the substrate in order to generate information indicative of the orientation of the substrate, and orienting the substrate based on information from the inspecting in order to ensure that said one of the first and second directions is parallel to the third direction.

* * * * *